(12) United States Patent
Frazee, Jr. et al.

(10) Patent No.: US 6,313,909 B1
(45) Date of Patent: Nov. 6, 2001

(54) FIBER DEFECT DETECTION APPARATUS AND METHOD

(75) Inventors: Ralph Edward Frazee, Jr., Bricktown; David Harry Smithgall, East Windsor, both of NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/295,297

(22) Filed: Apr. 20, 1999

(51) Int. Cl.[7] .................................................... G01N 21/00
(52) U.S. Cl. ............................................................ 356/73.1
(58) Field of Search .................................. 356/73.1, 239, 356/430, 237.1; 250/559.42, 559.43; 65/485–491; 385/147

(56) References Cited

U.S. PATENT DOCUMENTS

| | | | |
|---|---|---|---|
| 4,501,492 | * 2/1985 | Douklias | 356/73.1 |
| 5,469,252 | * 11/1995 | Doles et al. | 356/73.1 |
| 5,880,825 | * 3/1999 | Jakobsen et al. | 356/73.1 |

\* cited by examiner

Primary Examiner—Frank G. Font
Assistant Examiner—Tu T. Nguyen

(57) ABSTRACT

Methods and apparatus for detecting defects, such as air lines, in optical waveguide fibers are provided. The methods and apparatus employ scattered light interference signals produced by a fiber clad measurement system that transversely illuminates a fiber with a laser beam. Defects in the fiber produce characteristic peaks in the frequency spectrum of the scattered light signal. By filtering the scattered light signal to remove (a) the components associated with the fiber clad measurement system and (b) the fundamental component associated with the fiber, the defect-related components in the scattered light signal which represent defects in the associated fiber are determined. Once the presence of these defect-related components is determined, a defect detection output pulse is generated for each such event. The defect detection methods are also incorporated in an overall system for drawing and inspecting the optical lightguide fibers.

22 Claims, 6 Drawing Sheets

TYPICAL SPECTRUM FROM A FIBER WITH A 6 μm AIR LINE DEFECT

BAND PASS FILTER

AMPLITUDE OF SPECTRAL PEAKS FOR 6 MICRON DEFECT

SPECTRAL PEAKS LOCATIONS FOR 6 MICRON DEFECT

FIBER DEFECT DETECTION APPARATUS AND METHOD

FIELD OF THE INVENTION

This invention relates generally to methods and apparatus for detecting defects in optical lightguide fibers.

BACKGROUND OF THE INVENTION

The ability to detect defects in optical lightguide fibers is critical in providing high quality fiber and in devising manufacturing techniques that minimize the occurrence of such defects. Defects or inhomogenieties can affect the strength or transmission characteristics of the optical fiber. One class of defects, loosely defined as "bubbles" or "air lines", can range from the sub-micron ($\mu$m) to several microns in diameter and multiple-meter lengths. Although the term "air line" is used, defects can take on many different shapes and geometries. Defects over 10 $\mu$m in diameter can cause a variety of problems, including proof test breaks in the manufacturing process and fiber splice problems in the installation process.

Techniques for detecting defects in fibers (and, incidentally, dealing with the effects of defects on fiber diameter measurements) are known. See, for example, U.S. Pat. No. 4,046,536, issued Sep. 6, 1977, to D. H. Smithgall (analysis of fringe counts in the presence of "dropouts" resulting from faults in the fiber); U.S. Pat. No. 4,501,492, issued Feb. 26, 1985, to N. Douklias (detection of fiber defects and testing of fiber diameters using a spatial filter prepared using diffracted/scattered light from a defect-free fiber); and U.S. Pat. No. 5,185,636, issued Feb. 9, 1993, to L. J. Butten, et. al. (detection of fiber defects using light scattered from a fiber diameter measurement unit and performing Fast-Fourier-Transform (FFT) to examining the spectrum).

Although these techniques can detect defects in optical fibers, they nonetheless have several significant limitations, including cost and complexity. The added cost and complexity of such methods are due, in large part, to computational requirements and expenses associated with analyzing the frequency spectrum of light scattered signals, for example, performing a FFT on the light scattered signal repeatedly.

With increased market competition and heightened customer expectations, it has become important to develop a low-cost method to detect defects in optical fiber as it is drawn in the manufacturing process and deal with such defects in the fiber accordingly.

SUMMARY OF THE INVENTION

Cost and complexity of determining defects in lightguide fiber is significantly reduced in accordance with the principles of the present invention, by removing certain components of a scattered light signal, which represents an interference pattern received from a lightguide fiber clad diameter measurement system, and analyzing the modified scattered light signal. The modified scattered light signal is analyzed to determine if additional components are present and, in particular, so called defect-related components, the presence of these defect-related components being indicative of the presence of a defect in the associated fiber. Unlike prior fiber defect detection systems, the present invention obviates the need to compute and analyze the frequency spectrum of the scattered light signal. Accordingly, unnecessary expensive signal processing of the scattered light signal, such as digitizing and frequency transforms, is eliminated.

In one illustrative embodiment, a scattered light signal is filtered and the resulting signal is compared to a defect detection threshold to determine the presence of defect-related components in the scattered light signal, which in turn represent defects in the associated fiber. Specifically, the embodiment includes a filter to remove components of the scattered light signal associated with (a) the fiber clad diameter measurement system, such as the scan repetition rate, and (b) the fundamental component associated with the fiber clad diameter; a defect sensitivity adjuster to provide a detection threshold adjustment based on a reference signal; and a comparator to compare the bandpassed signal to the detection threshold to determine if a defect-related component is present, which represent defects in the associated fiber. Once the presence of a defect-related component is determined, the comparator generates a defect detection output pulse for each such event. These pulses can then be monitored and recorded by a fiber draw control computer, thereby creating a position and length record of the defects. This information can be used to simultaneously address both (1) the identity and removal of defects following the draw operation and (2) to determine the material quality of the fiber.

BRIEF DESCRIPTION OF THE DRAWINGS

The invention will be more fully understood from the following detailed description of illustrative embodiments taken in connection with the appended figures in which.

DETAILED DESCRIPTION

During the course of this description, like numbers are used to indicate like elements in the different figures that illustrate the invention.

Lightguide Fiber Clad Diameter Measurement Systems

The principles of the present invention are particularly useful with a lightguide fiber clad diameter measurement system in a fiber drawing device in which a transparent filament, such as a glass fiber, is drawn from an optical rod and the freshly drawn fiber is continuously inspected by the fiber clad diameter measurement system. The operation of lightguide fiber clad diameter measurement systems is based upon the interference to light rays which are either reflected from the surface of the fiber or refracted through the fiber when the fiber is illuminated normal to its axis with a laser beam. For further details see an article written by L. S. Watkins, entitled "Scattering From Side-Illuminated Glass Fibers for the Determination of Parameters," published in the Journal of the Optical Society of America, Vol. 64, June 1974, pp 767–772. Such fiber clad diameter measurements have been implemented in fiber measurement gauges, hereinafter "FM gauges." The so-called fiber clad diameter of an optical fiber is the outer diameter of the fiber and FM gauge measures the fiber clad diameter from a laser-generated scattered light signal that is representative of the fiber clad diameter which is detected by a scanned diode array. In particular, the FM gauge consists of an electronic signal processing unit and an optics unit containing the laser and detection electronics located on the draw tower that measures the fiber clad diameter. FM gauges are further described in an article written by D. H. Smithgall, L. S. Watkins and R. E. Frazee, entitled "High Speed Noncontact Fiber Diameter Measurement Using Forward Light Scattering," published in Applied Optics, Vol. 16, September, 1977, pp. 2395–2402.

Scattered Light Signal Patterns

Figure 1:
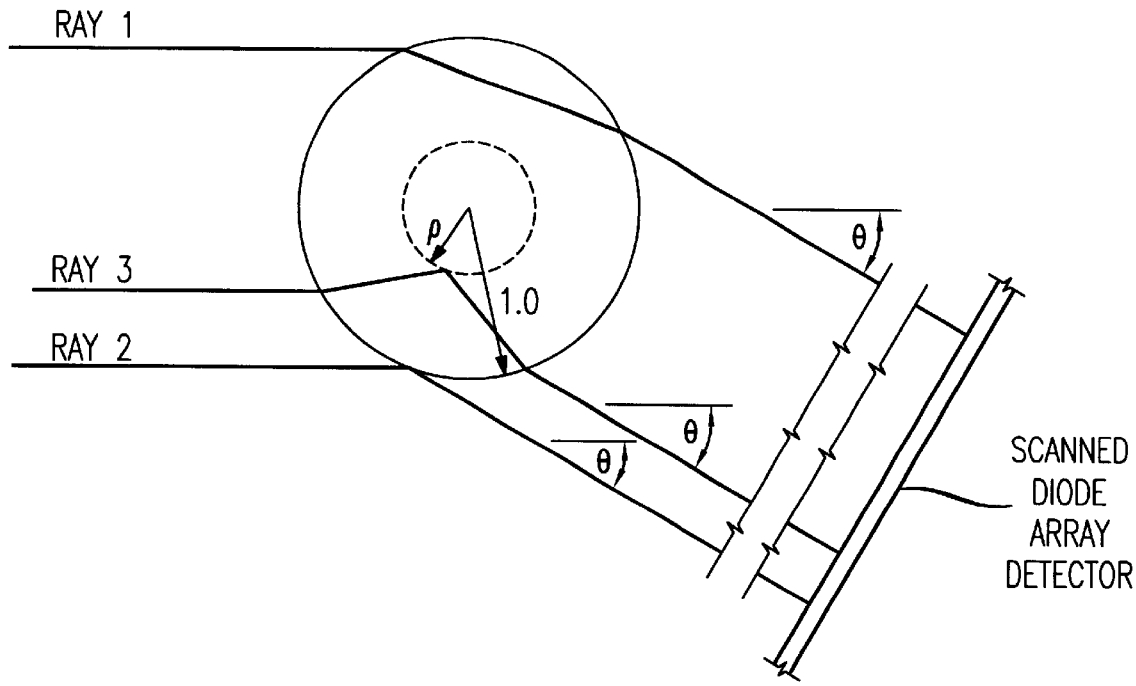
FIG. 1 shows a ray trace model of an optical fiber.

The defect detection technique of the present invention, like the aforementioned prior art defect detection schemes, involves using a scattered light signal generated by launching light rays into a fiber normal to its axis, as noted above. In the fiber of FIG. 1, incoming light rays which do not encounter or impinge on any defects, such as light rays 1 and 2, are scattered and interfere with each other. The fiber has particular interference characteristics and the scattered light signal is a function of those characteristics. In particular, as will be understood by persons skilled in the art, in an ideal fiber, the so called "far field" light from rays 1 and 2 is detected at an angle θ (other angles can be used) to generate the scattered light signal. Fiber clad diameter is determined from the phase characteristics of the scattered light signal. There is also amplitude modulation in the scattered light signal resulting from the modal structure of the laser, optics in the detection unit, and defects in the fiber. Typically, the frequency spectrum of a defect-free fiber contains two major components, which are represented in the frequency spectrum as two strong peaks. The first, for example, near 1 KHz, is the result of the scan repetition rate of the diode array used to gather samples of the scattered light signal. The second, for example, near 50 KHz, is the fundamental component associated with clad diameter measurement that depends upon a number of factors including: (a) the optical design of the system and (b) the clad diameter of the fiber. Those two components of the scattered light signal are hereinafter referred to as the "fiber diameter/measurement components."

A defect or inhomogeniety and, in particular, an air line in the fiber, affects both the amplitude and the phase characteristics of the scattered light signal. Although a defect distorts the phase characteristics of the scattered light signal, such changes in phase are difficult to measure and characterize. Consequently, phase measurement is not an advantageous technique for detecting defects in the fiber. However, identifying characteristic changes in the amplitude of the scattering pattern, by contrast, provides a good way of monitoring defects in the fiber.

Figure 2:
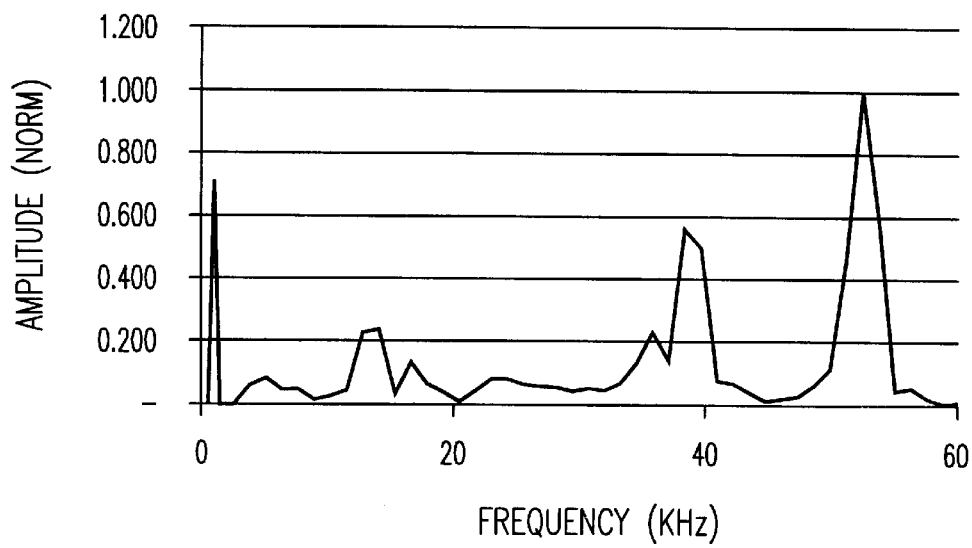
FIG. 2 shows the frequency spectrum of a scattered light signal relating to a fiber containing an air line defect with an estimated diameter of 6 $\mu$m.

Because an air line or other defect introduces amplitude modulation in the scattered light signal, additional spectral components appear therein. For example, FIG. 1 shows an air line, represented by a dashed line, of radius p centered on the axis of the fiber. An additional ray, ray 3, impinging on the air line, is refracted through the fiber and will interfere with the first two rays. The far field light of the refracted rays is detected at an angle θ to generate a scattered light signal. FIG. 2 shows a frequency spectrum of a scattered light signal computed from a fiber sample containing an air line defect with an estimated diameter of 6 μm. As can be seen from that FIG., the interference of rays 1 and 3, and the interference of rays 2 and 3 create two additional components between the aforementioned two fiber diameter/measurement system components, (e.g., 1 KHz and 50 KHz), which in this case are at 13 kHz and 39 kHz. More generally, when the normalized radius ρ is small, for instance, on the order of 0.02, the components are essentially collocated near 25 KHz. As ρ increases, the components separate and migrate toward 1 KHz and 50 KHz. This same ray trace model can be used to describe the generation of ray 3 from a small defect which is centered at a distance p from the center of the fiber. A similar effect occurs for other kinds of defect geometries and locations within the fiber.

Defect Detection Device

Accordingly, by detecting and isolating the aforementioned additional components, hereinafter referred to as "defect-related components," in a scattered light signal, defects in the associated fiber can be determined. Thus, in accordance with one aspect of the present invention, defects in a fiber are determined by (a) removing the fiber diameter/measurement components in the scattered light signal and (b) analyzing the resulting signal by comparing it to a defect detection threshold to determine whether defect-related components exist in the signal, which typically represent faults or defects in the associated fiber.

Figure 3:
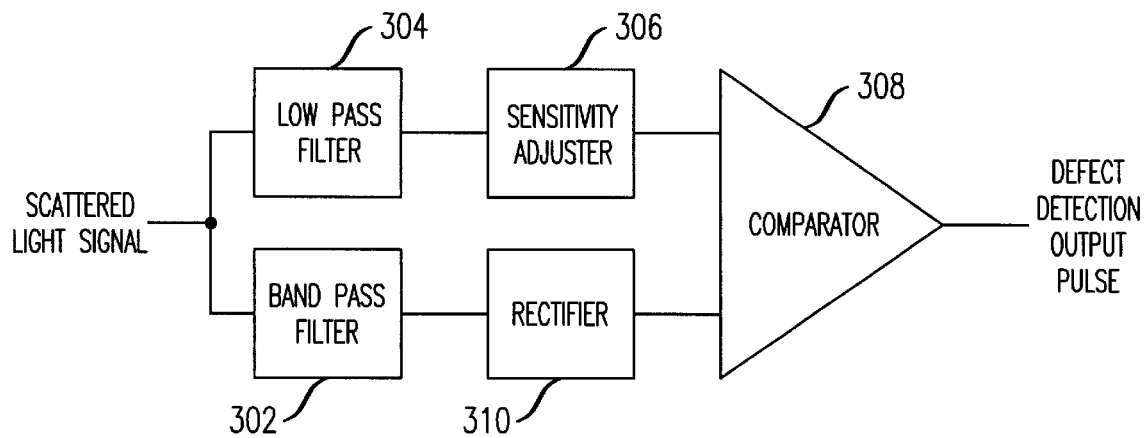
FIG. 3 is an illustrative embodiment, in block diagram form, of a defect detection device in accordance with the principles of the present invention.

FIG. 3 shows an illustrative embodiment, in block diagram form, of the defect detection device in accordance with the principles of the present invention. The device is implemented as an analog active circuit that includes a bandpass filter 302, a lowpass filter 304, a defect sensitivity adjuster 306, a rectifier 310, and a comparator 308.

The scattered light signal is passed through bandpass filter 302, which isolates the defect-related components in the scattered light signal by removing the fiber diameter/measurement components. The fundamental component will vary in proportion to the fiber diameter. For example, in FIG. 2 this component exists at 52 kHz for a 125 μm fiber. Once the scattered light signal is passed through the bandpass filter, the result is a periodic signal with no DC component. The output of the bandpass filter is then rectified by a rectifier 310, for example, a full-wave rectifier to provide a bipolar signal that captures the maximum signal amplitude from either polarity, or a half-wave rectifier to provide a unipolar signal. Alternatively (not shown), the output of the bandpass filter can be used without rectification, in which case, similar to a half-wave rectified signal, only one polarity of the periodic signal is used.

Figure 4:
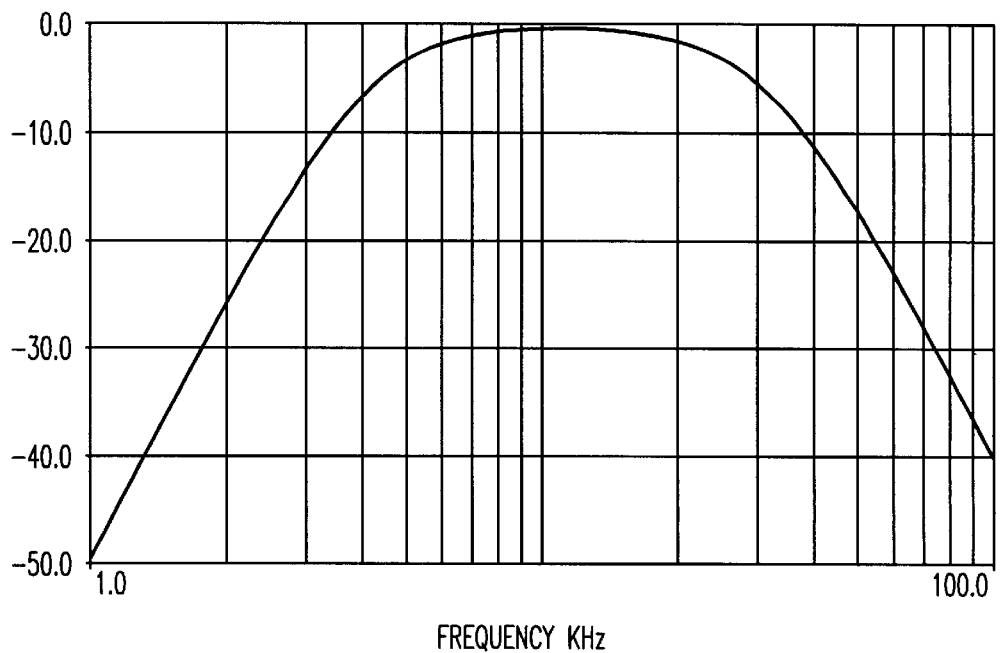
FIG. 4 is a graph of the transfer function of an exemplary bandpass filter used in the device of FIG. 3.

As shown in FIG. 4, an exemplary bandpass filter is modeled with an 8-pole analog Butterworth filter centered at 11 KHz. As a scattered light signal passes through the bandpass filter, the scan repetition rate component, for example, at 1 KHz, and the fundamental component, for example, at 50 KHz, are respectively suppressed –50dB and –18 dB, thereby, providing good signal-to-noise ratio with a relatively inexpensive and robust filter design.

Lowpass filter 304 is used to generate a reference signal, which is a DC voltage level that represents the total energy in the scattered light signal. Lowpass filter 304 has a predetermined gain and bandwidth, for example, a gain of 15 dB and a bandwidth of 250 Hz. Since the peak amplitude of the scattered light signal is proportional to its overall signal strength, use of such a reference voltage adjusts the defect detection threshold discussed below in proportion to the level of the overall signal strength. Thus, the use of lowpass filter 304 allows for accurate detection of defects independent of the strength of the scattered light signal. Moreover, the reference signal also changes in such a way as to take account of, and thereby, reduce or eliminate the effects of amplitude variations in the scattered light signal produced by oscillation of the fiber in the drawing process.

A sensitivity adjuster 306, for example, a potentiometer, is coupled to lowpass filter 304 for adjusting the defect detection threshold. Specifically, sensitivity adjuster 306 is used to attenuate the reference signal generated by lowpass filter 304 to provide only a portion thereof, for example, 10%, to comparator 308. This is necessary since the reference signal represents the peak amplitude component of the scattered light signal and other components, such as those representing defects, have smaller amplitudes. Thus, by using only an attenuated version of the reference signal as a defect detection threshold, the defect detection threshold is correctly scaled.

Thereafter, the bandpass-filtered signal is compared with the defect detection threshold in comparator 308. Based on the particular sensitivity adjustment, comparator 308 determines the presence of defect-related components in the passband signal that exceed the specified detection threshold, corresponding to fiber defects of a certain magnitude. If the detection threshold has been exceeded, comparator 308 provides a defect detection output pulse, which is then used for fiber monitoring or other manufacturing operations by a draw control computer or by an independent monitor not shown).

Figure 5:
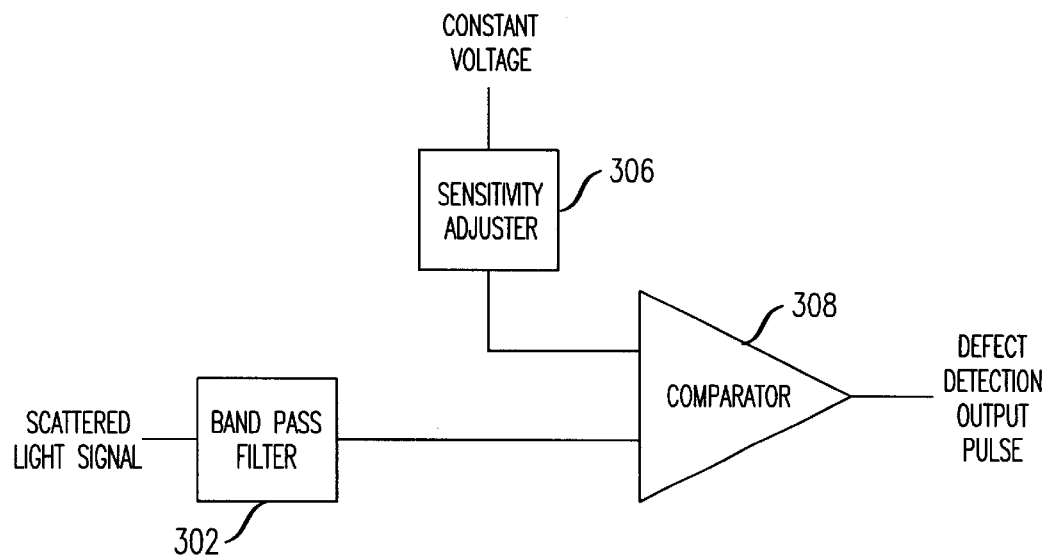
FIGS. 5 through 8 are other illustrative embodiments, in block diagram form, of a defect detection device in accordance with the principles of the present invention.

The reference signal can be generated by various other methods depending on a number of factors, including cost and type of application. For example, in the illustrative embodiment shown in FIG. 5, the reference signal for the defect detection threshold is generated by a constant voltage and then adjusted by the sensitivity adjuster 306.

Figure 6:
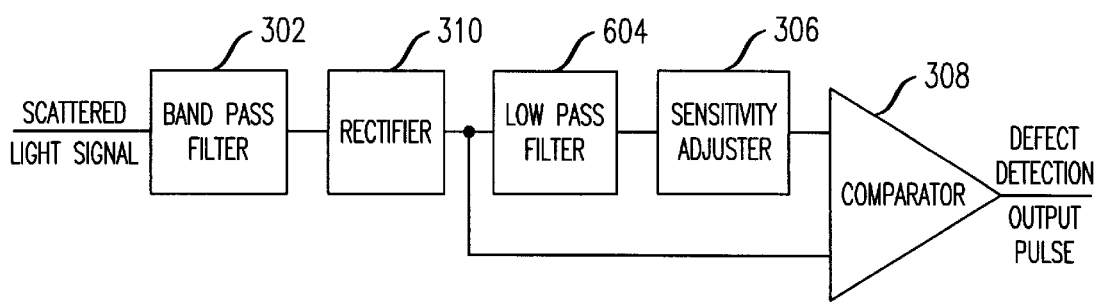

In still another illustrative embodiment, shown in FIG. 6, the reference signal is generated by passing the output of bandpass filter 302 through rectifier 310 and, thereafter, lowpass filter 604. This embodiment takes account of the fact that in the absence of a defect in the fiber, bandpass filter 302 will output background noise, which results from the non-ideal characteristics of the fiber and the fiber clad measurement system. A defect represents a relatively large, short duration amplitude spike from bandpass filter 302 that exceeds the average of this background noise. The reference level is then adjusted by sensitivity adjuster 306 before being compared to the output of rectifier 310 in comparator 308.

Figure 7:
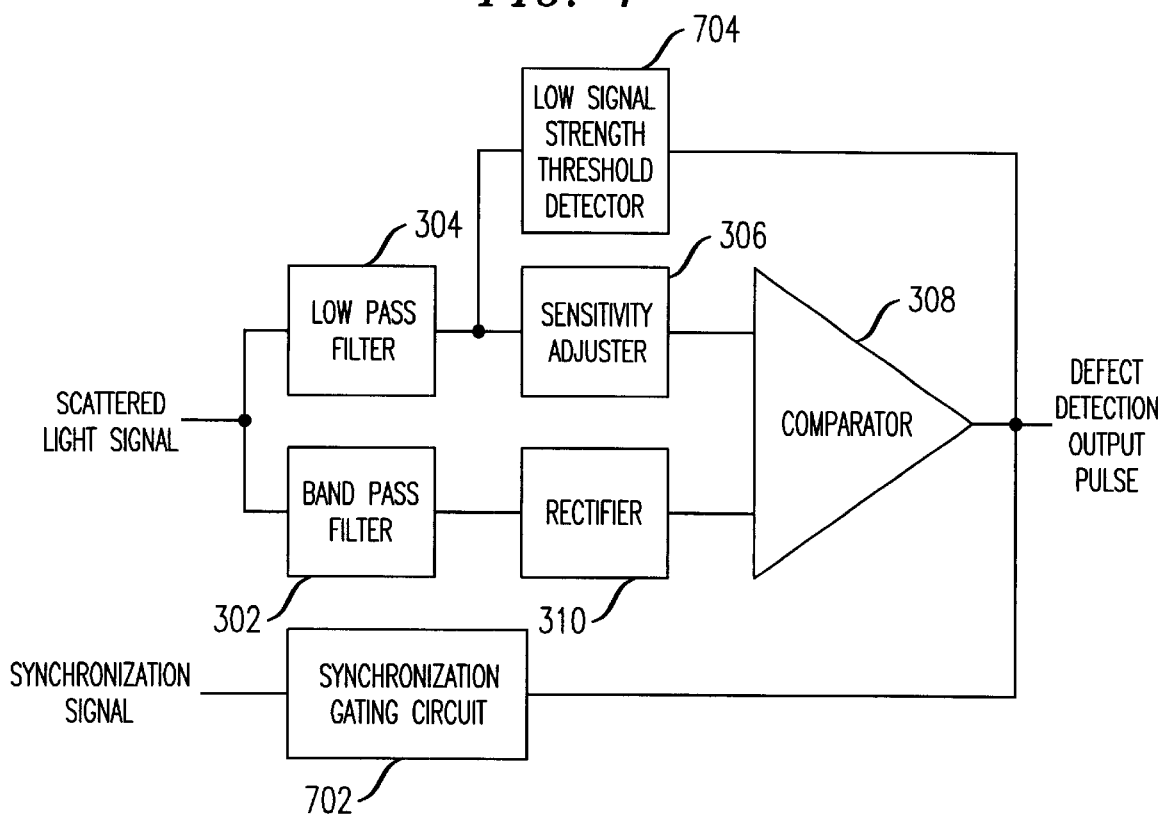

As shown in FIG. 7, a synchronization gating circuit 702 may be incorporated into the defect detection device to prevent erroneous defect detection output pulses from being generated during a portion of the measurement period. Such erroneous defect detection may result from the 1 KHz period of the scanned diode array detector in the fiber clad measurement system. In a scanned diode array, there is a blanking interval, for example, 5 microseconds, during which the scattered light signal amplitude is clamped to 0 volts, in effect exiting the bandpass filter with a 1 KHz square pulse train. While the fundamental frequency is suppressed, as discussed above, the harmonics pass through the filter, creating a damped transient disturbance to the scattered light signal. Synchronized gating circuit 702 receives a synchronization signal, for example, from a fiber clad measurement system, and uses this signal to eliminate the effect of the transient signal during the first portion of the scan interval.

Also shown in FIG. 7 is a low signal strength threshold detector 704 that may be incorporated into the defect detection device to prevent generation of defect detection output pulses when the lowpass signal strength falls below a predetermined fraction (for example 5%) of the normal scattered light signal strength. This condition can occur when there is no fiber in the fiber clad measurement system or the fiber is no longer in the laser beam.

Figure 8:
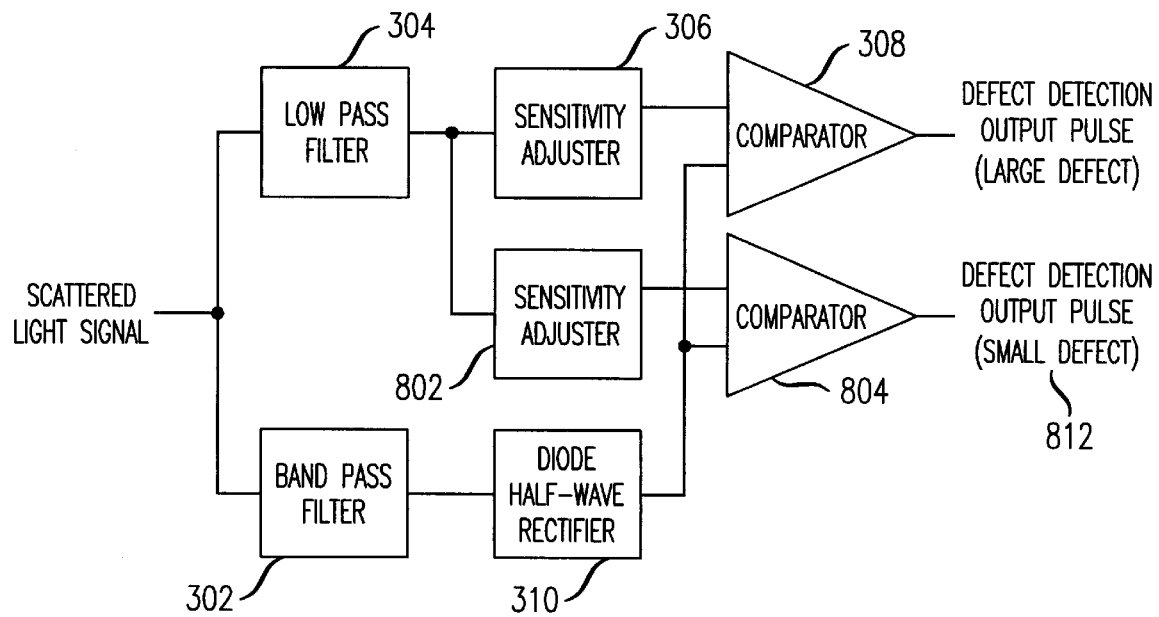

In another illustrative embodiment, shown in FIG. 8, the defect detection device can further include an additional comparator 804 and sensitivity adjuster 802. Thus, two levels of defect sensitivity are independently provided for, as shown by the presence of sensitivity adjusters 306 and 802, permitting multiple strategies for defect detection, as indicated by the respective defect detection output pulses of comparators 308 and 804. With the two independent sensitivity levels in the defect detection device, one level is adjusted to detect large diameter defects and the other adjusted to establish statistical patterns for small or moderately sized defects.

Many factors affect the ultimate detectability of defects in the fiber using the techniques described herein—something that those who may implement the invention may wish to keep in mind. For example, the detectability of randomly located defects depends upon (a) the defect diameter, (b) the position of the fiber, and (c) the orientation of the fiber, as the effective scattering cross-section of the defect changes with its position in the fiber. As the diameter of the defect decreases, the amplitudes of the defect-related components will also decrease, thus making defect detection more difficult.

Figure 9A:
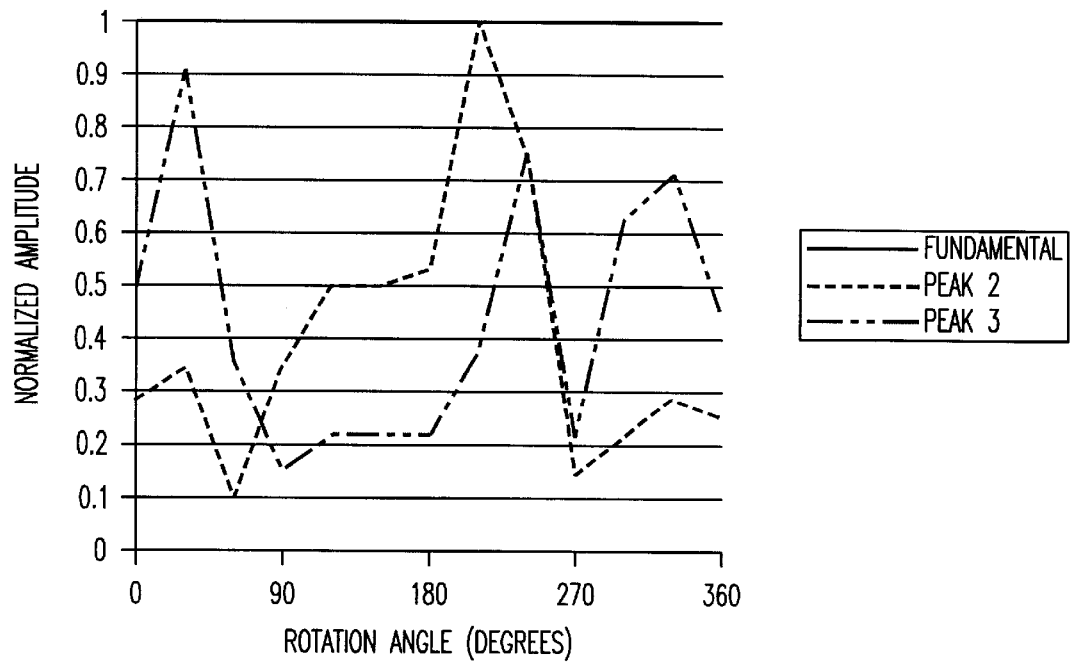
FIGS. 9A and 9B are respective graphs illustrating the effect of fiber orientation on the amplitude and frequency of the defect-related components of a scattered light signal relating to a fiber containing an air line defect with an estimated diameter of 6 $\mu$m.
Figure 9B:
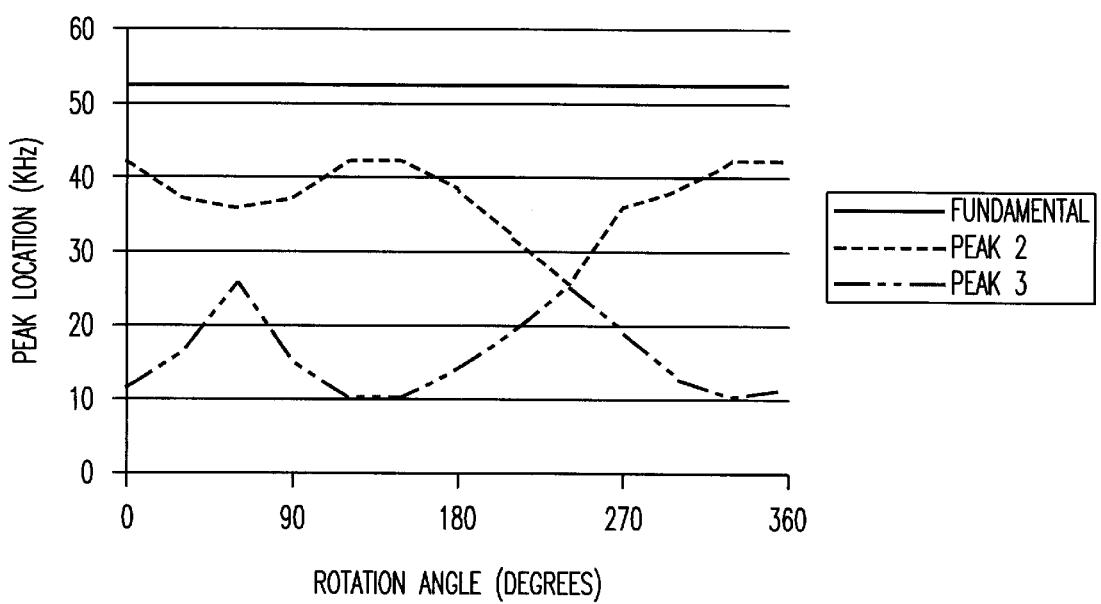

In order to illustrate the effect of fiber orientation upon the spectral content of the light scattering pattern the fiber corresponding to the frequency spectrum of the scattered light signal, shown in FIG. 2, with a 6 $\mu$m air line defect located 15 $\mu$m off the axis of the fiber, was rotated through 360 degrees with spectra computed at 30 degree intervals. Amplitude and frequency of the two strongest peaks are shown in FIGS. 9A and 9B, respectively. The amplitudes of the individual peaks vary over a 4:1 range and significant variation is observed in the spectral position of these peaks. In FIG. 9A, the output signal from the bandpass filter is minimal at an orientation near 270 degrees. This amplitude minimum in the spectrum establishes a minimum sensitivity for detection of this defect in this particular fiber.

Areas of Application

Figure 10:
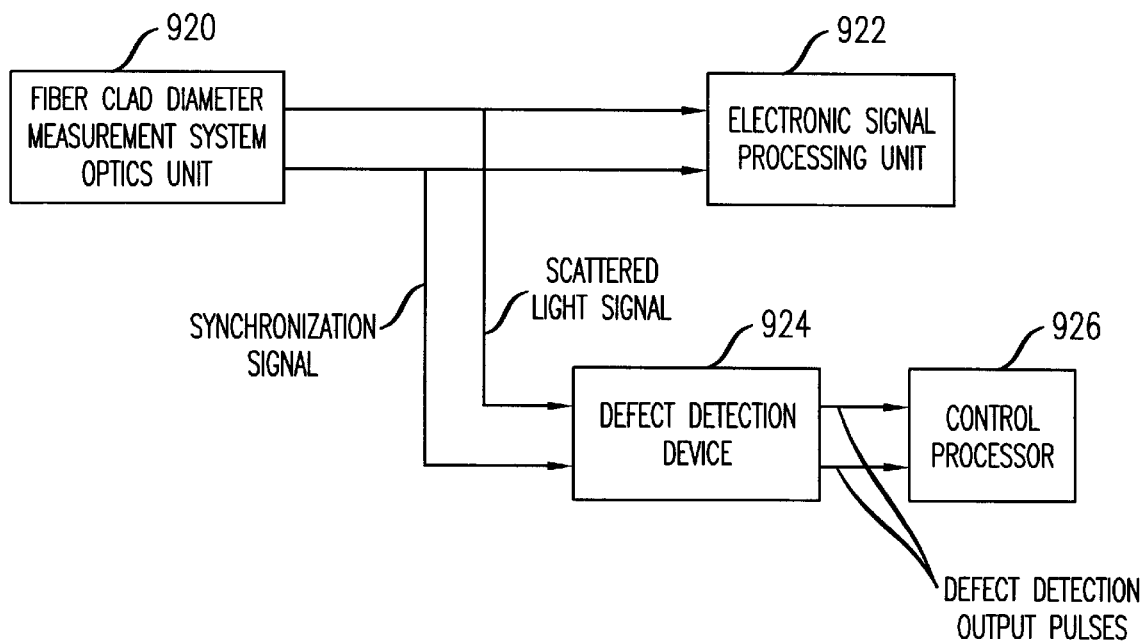
FIG. 10 shows a typical application of the defect detection device.

FIG. 10 illustrates a typical application of the defect detection device. The fiber clad diameter measurement system optics unit 920 is located on a draw tower (not shown) and the electronic signal processing unit 922 is located remotely in a control center (not shown). The scattered light-and synchronization signals from the fiber clad measurement system optics unit 920 are provided to defect detection device 924. Defect detection output pulses from defect detection device 924 may be input to any conventional control processor 926. Control processor 926 processes the defect detection output pulses as discussed above.

In such an application, the defect detection device has a number of important uses, including, of course, fiber defect detection and inspecting or monitoring the fiber quality being drawn on the draw tower. In particular, the existence and location (along the length of the fiber) of large and potentially problematic defects can be obtained by selecting an appropriate defect detection threshold via the sensitivity adjustments and measuring the duration that the detected event exceeds the defect detection threshold. Also, the defect detection device's defect detection output pulses are used to statistically monitor the quality of the fiber. By adjusting the defect detection threshold for "small" diameter air lines, typically less than 5 μm in diameter, a relative frequency of occurrence of such detected defects is established. This information is used, for example, to characterize the fiber quality and to support manufacturing statistical processing control.

Finally, it is to be understood that although the invention is disclosed herein in the context of particular illustrative embodiments, those skilled in the art will be able to devise numerous alternative arrangements. Thus, the invention is applicable to any system that, like a fiber clad diameter measurement system, produces a scattered light interference pattern signal by transversely illuminating a fiber with a laser beam. Such alternative arrangements, although not explicitly shown or described herein, embody the principles of the present invention and are thus within its spirit and scope.

We claim:

1. A method for detecting a defect in fibers that includes receiving a scattered light signal generated by a light source in a fiber diameter measurement system, the method comprising the steps of:

removing a first and second component of the scattered light signal to generate a modified scattered light signal, wherein the first component corresponds to the fiber diameter measurement system and the second component corresponds to the outer diameter of the fiber; and analyzing the modified scattered light signal to determine if a defect-related component of the scattered light signal is present, including generating a defect detection threshold which is a function of a reference signal; and comparing the modified scattered light signal to the detection threshold to determine if the defect-related component is present, the presence of the defect related component being indicative of the presence of a defect in the fiber.

2. The method of claim 1, wherein the reference signal is a constant voltage.

3. The method of claim 1, wherein the reference signal is generated by lowpass filtering the scattered light signal.

4. The method of claim 3, further including the step of rectifying the modified scattered light signal; and wherein the comparing step includes comparing the rectified modified scattered light signal to the detection threshold to determine if the defect-related component is present.

5. The method of claim 4, wherein the reference signal is generated by lowpass filtering the rectified modified scattered light signal.

6. The method of claim 5, including the step of eliminating the effect of a transient signal in the scattered light signal.

7. The method of claim 6, including the step of generating an output pulse when the defect-related component is present.

8. The method of claim 7, including the step of preventing generation of an output pulse when lowpass signal strength falls below a predetermined level.

9. A method for manufacturing lightguide fiber comprising the steps of:

drawing fiber on draw tower; and inspecting the fiber for defects, the inspecting step including the steps of, receiving a scattered light signal generated by a light source in a fiber diameter measurement system, the method comprising the steps of:

removing a first and second component of the scattered light signal to generate a modified scattered light signal, wherein the first component corresponds to the fiber diameter measurement system and the second component corresponds to the outer diameter of the fiber; and analyzing the modified scattered light signal to determine if a defect-related component of the scattered light signal is present, including generating a defect detection threshold which is a function of a reference signal; and comparing the modified scattered light signal to the detection threshold to determine if the defect-related component is present, the presence of the defect related component being indicative of the presence of a defect in the fiber.

10. The method of claim 9 comprising the further step of measuring the fiber clad diameter using said scattered light signal.

11. The method of claim 10, wherein the fiber diameter measurement system generates the scattered light signal in an optics unit on the draw tower.

12. The method of claim 11, wherein the optics units includes a diode array detector.

13. A fiber defect detection device which receives a scattered light signal from a light source in a fiber diameter measurement system, the device comprising a filter for removing first and second components of the scattered light signal to generate a modified scattered light signal, wherein the first component corresponds to the fiber diameter measurement system and the second component corresponds to the outer diameter of the fiber; and means for analyzing the modified scattered light signal to determine if a defect-related component of the scattered light signal is present, said means for analyzing including, a defect sensitivity adjuster to provide a defect detection threshold, wherein the defect detection threshold corresponds to a portion of a reference signal; and a comparator to compare the modified scattered light signal to the detection threshold to determine if the defect-related component is present, the presence of the defect-related component being indicative of the presence of a defect in the fiber.

14. The device of claim 13, wherein the reference signal is a constant voltage.

15. The device of claim 13, including a means for generating the reference signal.

16. The device of claim 15, wherein the means for generating the reference signal includes:

a lowpass filter to filter the scattered light signal to produce the reference signal.

17. The device of claim 13, including a rectifier for rectifying the modified scattered light signal; and wherein the comparator compares the rectified modified scattered light signal to the detection threshold to determine the defect-related component.

18. The device of claim 17, wherein the means for generating a reference signal includes a lowpass filter for filtering the rectified modified scattered light signal to produce the reference signal.

19. The device of claim 13, wherein the scattered light signal is generated by a clad diameter measurement system optics unit on a draw tower.

20. The device of claim 13, including a synchronization gating circuit for eliminating the effect of a transient signal in the scattered light signal.

21. The device of claim 20, including a pulse generator for generating an output pulse when the defect-related component is present.

22. The device of claim 21, including a low signal threshold detector to prevent the generation of the output pulse when the lowpass signal strength falls below a predetermined level.

* * * * *